United States Patent [19]

Hamasaki et al.

[11] Patent Number: 4,874,882
[45] Date of Patent: Oct. 17, 1989

[54] PROCESS FOR PREPARING MONOSODIUM PHOSPHOENOLPYRUVATE

[75] Inventors: Naotaka Hamasaki, Fukuoka; Hirotaka Kawamura, Ube; Norio Ohtsu, Ube; Ichiro Nakakoshi, Ube; Kikuo Ataka, Ube; Kiyosi Oomori, Ube; Masahiko Kouno, Ube, all of Japan

[73] Assignee: Ube Industries, Ltd., Ube, Japan

[21] Appl. No.: 27,631

[22] Filed: Mar. 18, 1987

[30] Foreign Application Priority Data

Mar. 25, 1986 [JP] Japan .................................. 61-64744
May 19, 1986 [JP] Japan ................................ 61-112482

[51] Int. Cl.$^4$ .............................................. C07F 9/09
[52] U.S. Cl. .................................... 558/131; 558/179; 260/398
[58] Field of Search ................. 558/131, 179; 260/389

[56] References Cited

U.S. PATENT DOCUMENTS 4,478,762 10/1984 Whitesides et al. ................. 558/131

OTHER PUBLICATIONS

J. Am Chem. Soc. 1985, pp. 7008–2027, Crans et al., Biochem. Prep., vol. 11, p. 101, 1966.

Chem. Ber., vol. 92, pp. 952–959, Friedrich Cramer et al.
Chem. Rev., vol. 61, pp. 607–608, Frieder W. Lichtenthaler.
Abstract of Japanese 113789, (1981).
Abstract of Japanese 500515, (1984).

Primary Examiner—Anton H. Sutto
Attorney, Agent, or Firm—Frishauf, Holtz, Goodman & Woodward

[57] ABSTRACT

Disclosed are a process for preparing monosodium phosphoenolpyruvate, which comprises subjecting monosodium monosubstituted phosphoenolpyruvate of Formula (I):

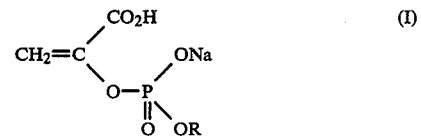

wherein, R represents an alkyl group, a cycloalkyl group or an aralkyl group,
to hydrolysis, and a use of monosodium phosphoenolpyruvate as a visceral function improver.

This invention provides a simple production process of monosodium phosphoenolpyruvate which is practicable on an industrial acale.

10 Claims, 4 Drawing Sheets

PROCESS FOR PREPARING MONOSODIUM PHOSPHOENOLPYRUVATE

BACKGROUND OF THE INVENTION

This invention relates to a process for preparing monosodium phosphoenolpyruvate and more particularly to a process for preparing monosodium phosphoenolpyruvate monohydrate, and use of the same as a visceral function improver.

Phosphoenolpyruvic acid (hereinafter referred to as PEP) is a phosphoric acid compound with high energy and particularly important compound, from the standpoint of biochemistry and enzymological chemistry, which produces adenosine-triphosphate (ATP) by reacting with adenocine-diphosphate (ADP).

Namely, in an organs or tissues of humans or other mammals, various disorders are caused if adenosine triphosphate is insufficient. For example, if an oxygen deficit due to ischemia is maintained in organs or tissues, the formation of ATP may become insufficient, resulting in causing morbidities such as cardiac infarction or renal insufficiency, respectively, in a heart or in a kidney. In order to cure such a disease, it is necessary to immediately supply tissue cells with ATP or any precursores thereof from outside of cells. But any substances useful for this purpose have not been found at all.

Accordingly, it has been desired to investigate a substance which is a high energy compound having good cell membrane permeability and capable of being intracellularly converted to a high energy compound such as ATP, and that can be a therapeutic agent for curing diseases, particularly an ischemic disease, more particularly an ischemic kidney disease or an ischemic heart disease, caused by the insufficiency of ATP, thereby aiming at effective utilization thereof as an improver for visceral functions.

Further, the above acid is used recently, in organic synthesis reactions utilizing enzyme catalysts (for example, *Journal of Amer. Chem. Soc.*, Vol. 107, p. 7008 and Vol. 107, p. 7019, 1985) and considered to be useful also as a blood preservative.

PEP and derivatives thereof have long been chemically synthesized, as exemplified by a method wherein a halopyruvic acid and a trialkyl phosphite are used. However, in these conventionally known synthesis, PEP is produced in the form of an ester, and there has not been found any satisfactory method for producing PEP on an industrial scale, in an unesterified form, as is present in the natural world.

As processes for preparing the unesterified PEP, the following processes have been proposed to date:

(1) A process wherein pyruvic acid protected by a trimethylsilyl group and a derivative of phosphoric acid are used (Japanese Provisional Patent Publication No. 113789/1981).

(2) A process wherein dialkylphosphoenolpyruvic acid is hydrolyzed and then monopotassium salt thereof is obtained by use of potassium hydroxide (Japanese Provisional Patent Publication No. 500515/1984).

(3) A process wherein monobenzylphosphoenolpyruvic acid is hydrogenolyzed (*Chem. Ber.*, Vol. 92, p. 952, 1959).

(4) A process wherein PEP cyclohexylamine salt is converted into PEP by use of an ion exchange resin, followed by addition of an alkali hydroxide to obtain an aqueous solution of an alkali metal salt of PEP (*Biochem. Prep.*, Vol. 11, p. 101, 1966).

In the above-described process (1), however, it is necessary to protect pyruvic acid with a trimethylsilyl group, and for said protection, trimethylsilyl chloride, which is costly, must be used. Moreover, the procedures employed therefor is complicated and PEP is formed as a trisodium salt. On the other hand, in the above-described process (2), while it can be expected that sodium salt of PEP may be obtained if sodium hydroxide is used instead of potassium hydroxide. After examination of such method, it was found that the monosodium salt of PEP with good purity could not be obtained. Further, in the above-described process (3), not only yield of monosodium salt of PEP produced is low but also the double bond in enol is hydro-genated to produce a large amount of by-products resulting in a complicated purification process. Also, in the above-described process (4), while there may be obtained an aqueous solution of an alkali metal salt of PEP, a product formed according to such a preparation method is unknown in its composition.

SUMMARY OF THE INVENTION

As has been described heretofore, an object of this invention is to provide a process for preparing PEP monosodium salt, which is practicable on an industrial scale, by overcoming the problems involved in the above-described processes for preparing PEP monosodium salt.

Another object of this invention is to utilize the above PEP monosodium salt prepared according to the above process, as a visceral function improver.

This invention relates to a process for preparing monosodium phosphoenolpyruvate which comprises subjecting monosodium monosubstituted phosphoenolpyruvate of Formula (I):

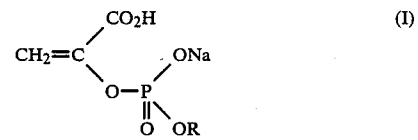

wherein, R represents an alkyl group, a cycloalkyl group, or an aralkyl group,
to hydrolysis, and also to a use of the above monosodium phosphoenolpyruvate prepared according to the above process as a visceral function improver, particularly for an ischemic disease, more particularly for an ischemic kidney disease or an ischemic heart disease.

DETAILED DESCRIPTION OF THE PREFERRED EMBODIMENTS

Figure 1:
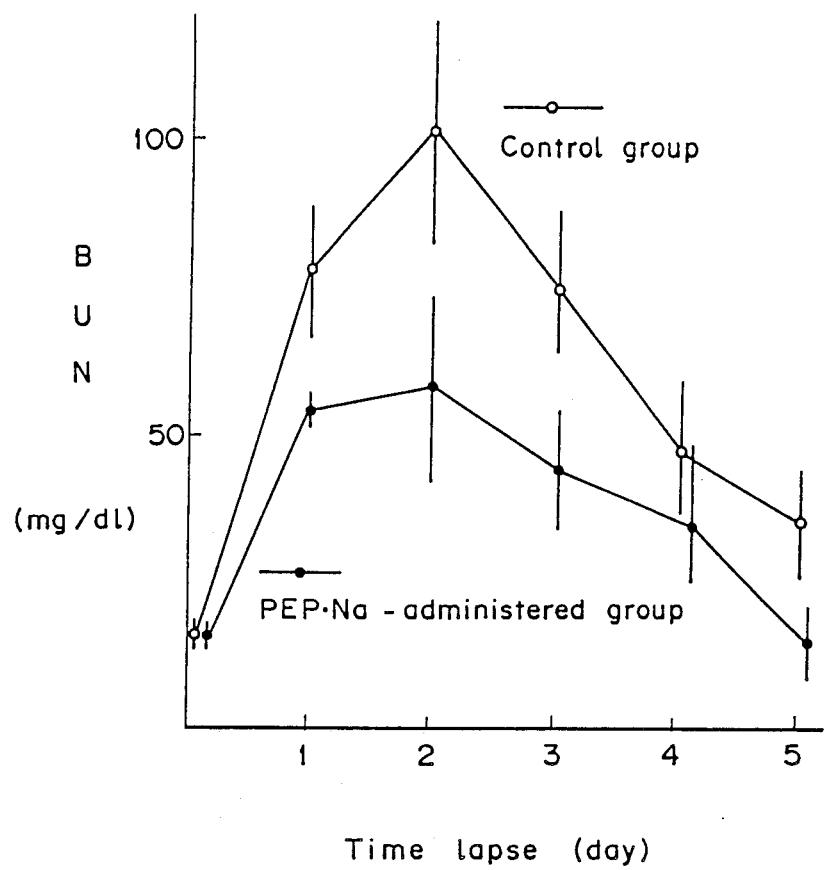
FIG. 1 is a graph showing how BUN in blood changes with time lapse when an injection comprising monosodium phosphoenolpyruvate monohydrate or a physiological saline was respectively intravenously administered to renal arteriae of rabbits by blocking blood flow thereof and before release of blocking.

In this invention, when R represents an alkyl group, the alkyl group may not particularly be limited by the number of carbon atoms contained therein and may be straight or branched. Such alkyl groups may specifically include, for example, a methyl group, an ethyl group, a n-propyl group, an isopropyl group, a n-butyl group, an isobutyl group, a sec-butyl group, a tert-butyl group, a n-amyl group, an isoamyl group, a sec-amyl group, an active amyl group, a tert-amyl group, a n-hexyl group, an isohexyl group, a 3-methylpentyl group, a neo-hexyl group, a 2,3-dimethylbutyl group, etc., and preferably a methyl group, an ethyl group, a n-propyl group and an isopropyl group.

When R represents a cycloalkyl group, the cycloalkyl group also may not particularly be limited by the number of carbon atoms contained therein and may be unsubstituted or substituted. Such alkyl groups may specifically include, for example, a cyclopropyl group, a cyclobutyl group, a 1-methyl-cyclopropyl group, a 2-methylcyclopropyl group, a cyclopentyl group, a 1-methylcyclobutyl group, a 2-methylcyclobutyl group, a 1,2-dimethylcyclopropyl group, a 2,2-dimethylcyclopropyl group, a 1-ethylcyclopropyl group, a 2-ethylcyclopropyl group, a cyclohexyl group, a 1-methylcyclopentyl group, a 2-methylcyclopentyl group, a 3-methylcyclopentyl group, a 1,2-dimethylcyclobutyl group, a 1,3-dimethylcyclobutyl group, a 2,2-dimethylcyclobutyl group, a 2,3-dimethylcyclobutyl group, a 3,3-dimethylcyclo-butyl group, a 1-ethylcyclobutyl group, a 2-ethylcyclobutyl group, a 3-ethylcyclobutyl group, 1-propylcyclopropyl group, a 2-propylcyclopropyl group, a 1-methyl-2-ethylcyclopropyl group, a 1-ethyl-2-methylcyclopropyl group, etc., and preferably a cyclopentyl group, a cyclohexyl group, a cycloheptyl group, etc.

Further, when R represents an aralkyl group, the aralkyl group also may not particularly be limited by the number of carbon atoms contained therein and such aralkyl group may be unsubstituted or substituted. Such aralkyl groups may be exemplified by an aralkyl group whose aromatic nucleus is unsubstituted such as a benzyl group, a diphenylmethyl group, a triphenylmethyl group, etc. and an aralkyl group whose aromatic nucleus is substituted such as an o-chlorobenzyl group, a p-chlorobenzyl group, a m-chlorobenzyl group, an o-methylbenzyl group, a p-methylbenzyl group, a m-methylbenzyl group, etc., and preferably a benzyl group.

The above monosodium monosubstituted phosphoenolpyruvate of Formula (I) can be obtained by reacting a disubstituted phosphoenolpyruvic acid of

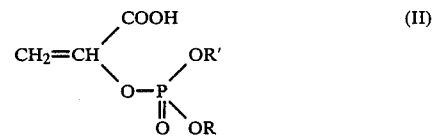

wherein R and R' may be the same or different and each represent an alkyl group, a cycloalkyl group or an aralkyl group as defined above for R, with sodium iodide.

Those compounds represented by the above Formula (II) can be obtained, for example, by reacting a halopyruvic acid with a phosphite of Formula (III):

wherein R, R' and R" may be the same or different and each represent an alkyl group, a cycloalkyl group or an aralkyl group as defined above for R and R', respectively, (Chem. Rev., Vol. 61, p. 607, 1961).

The process for preparing the material of monosodium monosubstituted phosphoenolpyruvate of Formula (I) summarized above may be illustrated by the following reaction scheme:

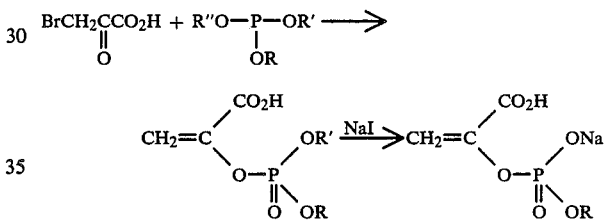

In this invention, monosodium monosubstituted phosphoenolpyruvate of Formula (I) to be obtained according to the above-described preparation process, etc., is subjected to hydrolysis in water or an aqueous solution. As the above aqueous solution, there may be used a mixed solvent comprising water as a primary component and an organic solvent, for example, a mixed solution of water/alcohol such as a mixed solution of water/methanol, a mixed solution of water/ethanol, etc., or a mixed solution of water/acetone, a mixed solution of water/tetrahydrofuran, etc. The amount of water to be employed in the above solutions may suitably be varied depending on the kind of the substituent in monosodium monosubstituted phosphoenolpyruvate, and usually it is preferable to employ it in an amount of 1.5 to 10 times the monosodium monosubstituted phosphoenolpyruvate employed. Reaction temperature may also be varied depending on the kind of the substituent, and usually is 5° to 50° C., preferably 20° to 40° C. Reaction time is dependent on the kind of the substituent, amount of water, reaction temperature, etc., and usually 5 to 72 hours is preferable.

In order to precipitate the monosodium phosphoenolpyruvate from water or an aqueous solvent in the form of a monohydrate after completion of hydrolysis, there may be added a water-soluble organic solvent, for example, acetone, methanol, ethanol, acetonitrile, tetrahydrofuran, dioxane, etc. to the resulting hydrolyzed solution; wherein the organic solvent may be preferably employed in an amount of 2 to 10 times the amount of water employed for hydrolysis in terms of volume ratio. The crystal thus precipitated may be isolated according to any customary method such as filtration etc., followed by drying by means of, for example, air drying, etc. The thus obtained crystal was subjected to identification under NMR spectroscopy (solvent: heavy water; internal standard: hydroquinone), high performance liquid chromatography (column; TSK gel QSA-2SW; eluent: 0.15 M aqueous KCl; detecter: UV 210 nm; internal standard; maleic acid) and atomic absorption spectroscopy and it was found to be monosodium phosphoenolpyruvate monohydrate.

In this invention, the above monosodium phosphoenolpyruvate, particularly monohydrate thereof is effective as the visceral function improver.

Further, a phosphoenolpyruvic acid, a salt thereof and a derivative thereof represented by Formula (I)' shown below:

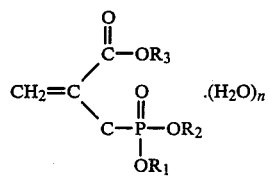

(I)' wherein $R_1$, $R_2$ and $R_3$ each independently represent a hydrogen atom, a sodium atom, a straight or branched alkyl group having 1 to 18 carbon atoms, or a cycloalkyl group having 5 to 7 carbon atoms; and n is 0 to 6. are also effective as the visceral function improver.

In the above Formula (I)', when $R_1$, $R_2$ and $R_3$ each independently represent a straight or branched alkyl group having 1 to 18 carbon atoms, they include specifically a methyl group, en ethyl group, a n-propyl group, an isopropyl group, a n-butyl group, an isobutyl group, a sec-butyl group, a tert-butyl group, a n-amyl group, an isoamyl group, a sec-amyl group, an active amyl group, a tert-amyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a heptadecyl group, a n-octadecyl group, etc.

When $R_1$, $R_2$ and $R_3$ each represent a cycloalkyl group having 5 to 7 carbon atoms, they include specifically a cyclopentyl group, a cyclohexyl group, a 1-methylcyclopentyl group, a 2-methylcyclopentyl group, a 3-methylcyclopentyl group, a cycloheptyl group, 1-methylcyclohexyl group, a 2-methylcylcohexyl group, a 3-methylcylcohexyl group, a 4-methylcylcohexyl group, 1-ethylcyclopentyl group, 2-ethylcyclopentyl group, 3-ethylcyclopentyl group, a 1,2-dimethylcyclopentyl group, a 1,3-dimethylcyclopentyl group, a 2,2-dimethylcyclopentyl group, a 2,3-dimethylcyclopentyl group, a 3,3-dimethylcyclopentyl group, etc.

In Formula (I)', a compound wherein $R_1$ is sodium, $R_2$ and $R_3$ each are a hydrogen atom at the same time and n is 1 corresponds to the above monosodium phosphoenolpyruvate monohydrate.

In the visceral function improver of this invention, the monosodium phosphoenolpyruvate represented by the above Formula (I), can be used alone or in combination with other solid or liquid medicinal carriers, and other medicinal components or diluents, namely, additives such as an excipient and a stabilizer. In other words, the visceral function improver of this invention may be orally administered in the form of granules, fine granules, powders, tablets, hard capsules, soft capsules, syrups, milks, suspensions, solutions, etc., or may be intravenously, intramuscularly or hypodermicly administered as an injection or an infusion preparation. It also can be used in the form of suppositories, collunariums, eye drops or inhalants as preparations for local administration to a rectum, a nose, eyes or lungs. Also, it may be used as powder for injection which can be used by making a preparation when administered. To prepare the visceral function improver of this invention, it is also possible to use organic or inorganic, solid or liquid carriers or diluents used for medicines suited for oral, rectal, parenteral or local administration. As the excipient used when solid preparations are produced, there can be used, for example, lactose, sucrose, starch, talc, cellulose, dextrin, kaolin, calcium carbonate, etc. Liquid preparations for oral administration, i.e., milks, syrups, suspensions, solutions, etc. may contain an inert diluent, for example, water, vegetable oil, etc. generally used. Such preparations may also contain, besides the inert diluent, auxiliary agents such as a wetting agent, a suspension auxiliary, an edulcorant, a flavoring agent, a coloring agent and a preservative. The preparations may also be liquid preparations to be contained in a capsule made of a substance capable of being absorbed, for example, such as gelatin. Solvents or suspension agents used for the production of the preparations for parenteral administration, i.e., injections, suppositories, collunariums, eye drops and inhalants, may include, for example, water, propylene glycol, polyethylene glycol, benzyl alcohol, ethyl oleate, lecithin, etc. Bases used for the suppositories may include, for example, cacao butter, emulsified cacao butter, laurin butter, witepzole, etc. The preparations may be prepared according to conventional methods.

The clinical dose may be such that, when orally administered, a preparation is administered usually with a dose of 0.1 to 1000 mg/kg (body weight; b.d.), preferably 1 to 800 mg/kg (b.d.), of the active component per day to an adult, but, more preferably, the dose may be suitably increased or decreased according to age, pathology and symptoms. The above dose per day is a dose for the administration which may be made once a day, twice or three times a day with suitable intervals, or intermittently.

Also, when used as an injection, a preparation is preferably administered continuously or intermittently with a dose of 1 to 400 mg/kg (b.d.) of the active component per one time to an adult.

EXAMPLE

Hereinafter, this invention will be described in more detail based on Reference example, Examples and Test Examples.

Reference Example

To a solution of trimethylphosphite (6.8 g) in anhydrous ether (40 ml) was added dropwise to a solution of bromopyruvic acid (8.4 g) in anhydrous ether (20 ml), with stirring, at a rate such that the ether may be refluxed slowly. After completion of the addition, the resulting solution was further reacted for 1 hour, and the reaction mixture was concentrated under reduced pressure to give a viscous liquid. The liquid obtained was dissolved in 60 ml of methyl ethyl ketone, and to the resulting solution was added 7.5 g of sodium iodide, followed by stirring at 10° C. or lower for 6 hours. The crystal thus precipitated was filtered out, washed with a small amount of methyl ethyl ketone and dried under reduced pressure to give 9.8 g of monosodium monomethyl phosphoenolpyruvate.

Example 1

In 19.6 ml of water was dissolved 9.8 g of monosodium monomethyl phosphoenolpyruvate, and the resulting solution was stirred at 25° C. for 30 hours. After completion of the reaction, 98 ml of acetone was added to the solution and the mixture was cooled to 0° C. The crystal thus precipitated was filtered out and dried under reduced pressure. The analysis of the crystal was conducted by measuring melting point and by means of NMR spectroscopy, IR spectroscopy and elemental analysis and it was confirmed that the crystal was monosodium phosphoenolpyruvate monohydrate. Yield: 7.2 g m.p. 120° C. (decomp.)

Purity of the crystal was found to be 99.3% according to the analysis by means of high performance liquid chromatography.

Na value:
Found: 11.03%
(Calculated): 11.05%)

Example 2

The same procedure as in Example 1 was repeated except that acetone used as a solvent for crystallization was replaced by ethanol.
Yield: 6.9 g
m.p.: 120° C. (decomp.)
Purity (high performance liquid chromatography): 99.0%
Na analysis: 11.10%

Example 3

The same procedure as in Example 1 was repeated except that monosodium monobenzyl phosphoenolpyruvate obtained by means of the same method as in Reference example was used.
Yield: 6.8 g
m.p.: 120° C. (decomp.)
Purity: 98.9%
Na analysis: 11.12%

Example 4

Production of an injection containing monosodium phosphoenolpyruvate

One gram (1 g) of monosodium phosphoenolpyruvate monohydrate was precisely weighed and dissolved in distilled water for injection. Subsequently, using 0.1N NaOH, the solution was adjusted to the pH of about 7. Thereafter, the solution was poured into a measuring flask, where the volume was made to 100 ml, and filtered with use of a membrane filter having a pore size of 0.22μ to prepare an injection of monosodium phosphoenolpyruvate monohydrate.

Test Example 1

Effect on ischemic kidney of rabbit

The animals used in this experiment were 10 male Japanese white-strain rabbits, and were grouped into a group of 5 rabbits to which the injection of monosodium phosphoenolpyruvate (hereinafter simply called "PEP·Na") prepared in Example 4 should be administered and a group of 5 rabbits to which a physiological saline should be administered, to carry out experiments as follows:

To each of the rabbits used in this experiment, a 1% aqueous solution of pentobarbital sodium was intravenously injected in an amount of 3 ml/kg (b.w.) to apply general anesthesia, and a median incision of its venter was carried out to extirpate the right kidney. Subsequently, the left kidney was exposed to infiltrate xylocaine into the surrounding portion of the renal pelvis, and the left renal artery was blocked while handling the kidney with tender care. More specifically, the blood flow of the renal artery was blocked for 60 minutes, and then released for 10 minutes, followed by blocking for more 60 minutes, to perform ischemia for 120 minutes in total. Thereafter, blocking was released for reperfusion. During these procedures, to the rabbits belonging to the PEP·Na group, PEP·Na was intravenously administered in the form of an injection prepared in Example, with a dose of 10 mg/kg (b.w.) every time immediately before release of the first and the second blocking, and, also after release of the blocking, PEP·Na was similarly administered with a dose of 10 mg/kg (b.w.) once a day. On the other hand, to the rabbits belonging to the control group, a physiological saline was intravenously administered in an amount of 1 ml/kg (b.w.) every time immediately before release of the first and the second blocking, and, also after release of the blocking, the physiological saline was similarly administered in an amount of 1 ml/kg (b.w.) once a day, every day.

Next, blood urea nitrogen (hereinafter "BUN") and creatinine value which are standards to know the morbidity of a kidney were assayed with time to make an index showing the recovery rate of renal function. Results obtained are shown in Table 1 and Table 2 and also in FIG. 1 and FIG. 2.

TABLE 1

| | Change in BUN with time | |
|---|---|---|
| Time lapse (day) | BUN of rabits in PEP.Na-administered group (mg/dl) | BUN of rabbits in control group (mg/dl) |
| Immediately before blocking | 14.5 ± 1.3 | 15.2 ± 0.9 |
| After 1 day | 54.2 ± 2.2 | 77.7 ± 10.8 |
| After 2 days | 58.0 ± 15.2 | 100.6 ± 18.5 |
| After 3 days | 44.1 ± 10.5 | 74.4 ± 12.3 |
| After 4 days | 35.5 ± 11.0 | 46.8 ± 11.2 |
| After 5 days | 15.0 ± 5.8 | 35.2 ± 9.6 |

TABLE 2

| | Change in creatinine value with time | |
|---|---|---|
| Time lapse (day) | Creatinine value of rabbits in PEP.Na-administered group (mg/dl) | Creatinine value of rabbits in control group (mg/dl) |
| Immediately before blocking | 1.18 ± 0.06 | 1.26 ± 0.46 |
| After 1 day | 2.83 ± 0.74 | 5.13 ± 0.84 |
| After 2 days | 2.61 ± 0.87 | 4.96 ± 0.80 |
| After 3 days | 2.06 ± 0.72 | 3.36 ± 0.65 |
| After 4 days | 1.73 ± 0.40 | 2.28 ± 0.44 |
| After 5 days | 1.19 ± 0.17 | 1.78 ± 0.32 |

Apparently, according to Table 1 and FIG. 1, in the rabbits in PEP·Na-administered group, there is shown a significantly lower value of BUN in 1 day (24 hours) after release of blocking, as compared with the rabbits in control group, which value gradually decreases thereafter over a period of 4 days and gets back to the value given before blocking earlier than in control group of rabbits.

Figure 2:
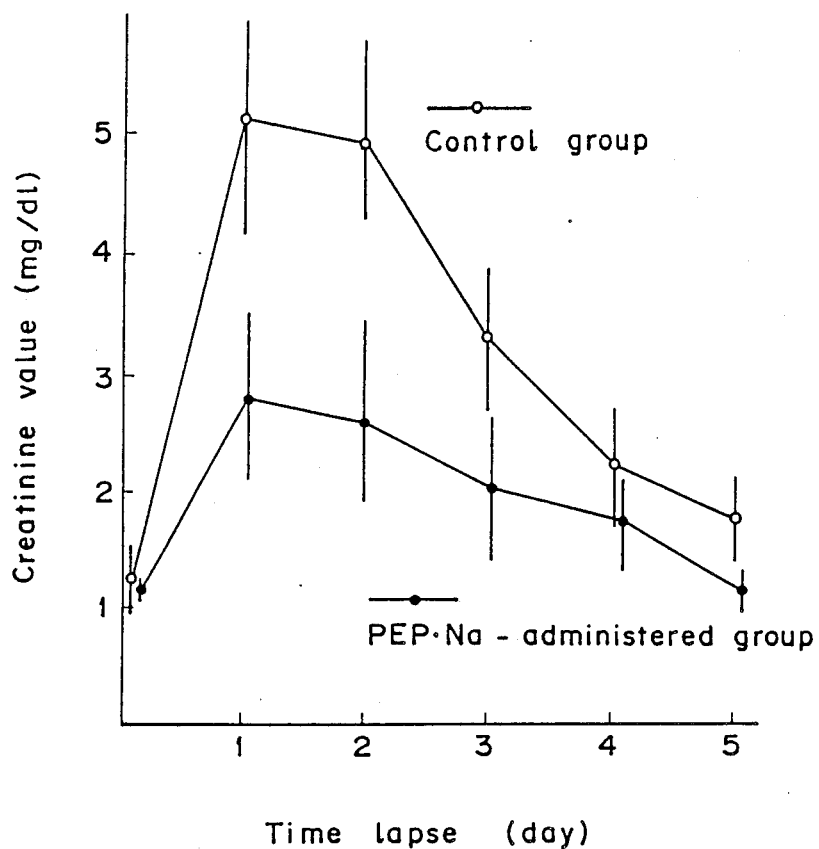
FIG. 2 is a graph showing how the value of creatinine in blood changes with time lapse when an injection comprising monosodium phosphoenolpyruvate monohydrate or a physiological saline was respectively intravenously administered to renal arteriae of rabbits by blocking blood flow thereof and before release of blocking.

As will be also apparent from Table 2 and FIG. 2, in the rabbits in PEP·Na-administered group, there is also shown a significantly lower value of creatinine in 1 day (24 hours) after release of blocking, as compared with the rabbits in control group, which value gradually decreases thereafter over a period of 4 days and gets back to the value before blocking earlier than in control group of rabbits.

Accordingly, it has been confirmed that PEP·Na is apparently effective for the recovery of renal function of a rabbit.

Test Example 2

Effect on ischemic kidney of beagle

The animals used in this experiment were 6 male beagles, and were grouped into a group of 3 beagles to which the injection of PEP·Na prepared in Example should be administered and a group of 3 beagles to which a physiological saline should be administered, to carry out experiments as follows in the same manner as in Test Example 1.

To each of the beagles, a 5% aqueous solution of pentobarbital sodium was intravenously injected in an amount of 0.5 ml/kg (b.w.) to apply general anesthesia, and a median incision of its venter was carried out to extirpate the right kidney. Subsequently, the left kidney was exposed to infiltrate xylocaine into the surrounding portion of the renal pelvis, and the blood flow of the left renal artery was blocked for 90 minutes while handling the kidney with tender care. Thereafter, blocking was released for reperfusion. To the beagles belonging to the PEP·Na administered group, PEP·Na was intravenously administered in the form of an injection prepared in Example, with a dose of 100 mg/kg (b.w.) every time immediately after release of blocking, and, also, thereafter, PEP·Na was similarly administered with a dose of 100 mg/kg (b.w.) once a day every day. On the other hand, to the beagles belonging to the control group, physiological saline was intravenously administered in an amount of 10 ml/kg (b.w.) every time immediately after release of blocking, and, also thereafter, physiological saline was similarly administered in an amount of 10 ml/kg (b.w.) once a day.

Next, BUN and creatinine value were assayed with time to make an index showing the recovery rate of renal function. Results obtained are shown in Table 3 and Table 4 and also in FIG. 3 and FIG. 4.

TABLE 3

| | Change in BUN with time | |
|---|---|---|
| Time lapse (day) | BUN of beagles in PEP.Na-administered group (mg/dl) | BUN of beagles in control group (mg/dl) |
| Immediately before blocking | 15 ± 0.5 | 15 ± 1.2 |
| After 1 day | 46 ± 8.3 | 83 ± 12.1 |
| After 2 days | 63 ± 10.1 | 155 ± 18.4 |
| After 3 days | 52 ± 9.6 | 203 ± 23.5 |
| After 4 days | 44 ± 9.2 | 210 ± 25.0 |

TABLE 4

| | Change in creatinine value with time | |
|---|---|---|
| Time lapse (day) | Creatinine value of beagles in PEP.Na-administered group (mg/dl) | Creatinine value of beagles in control group (mg/dl) |
| Immediately before blocking | 0.8 ± 0.23 | 0.4 ± 0.10 |
| After 1 day | 3.0 ± 0.45 | 4.1 ± 0.45 |
| After 2 days | 2.9 ± 0.41 | 6.9 ± 0.60 |
| After 3 days | 2.5 ± 0.33 | 8.4 ± 0.73 |
| After 4 days | 2.0 ± 0.31 | 8.7 ± 0.81 |

Figure 3:
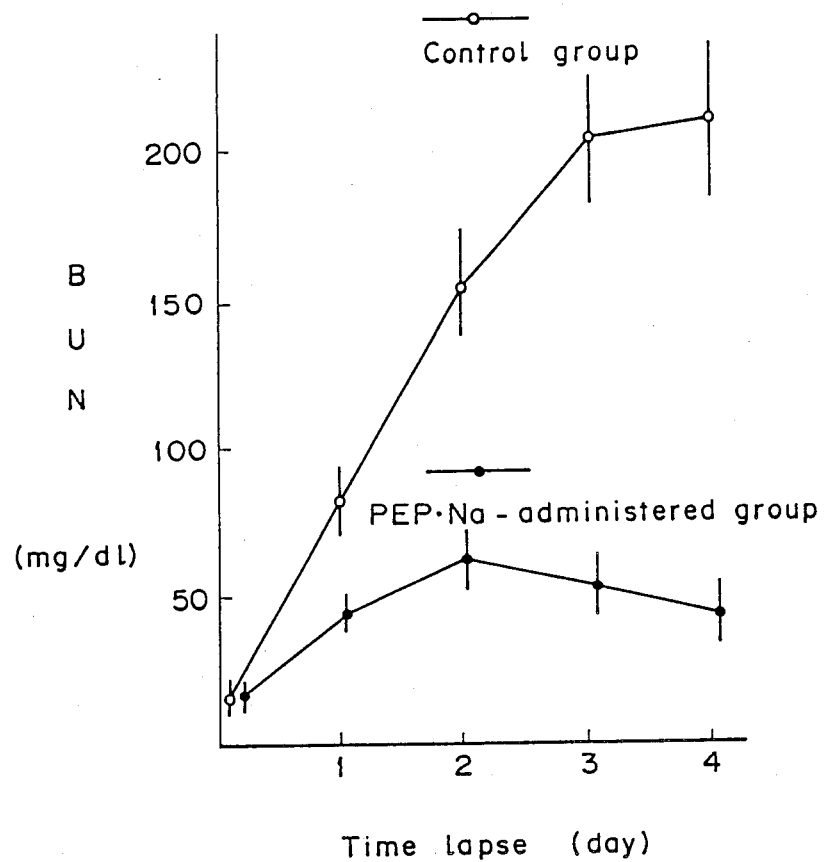
FIG. 3 is a graph showing how BUN in blood changes with time lapse when an injection comprising monosodium phosphoenolpyruvate monohydrate or a physiological saline was respectively intravenously administered to left renal arteriae of beagles by blocking them and after release of blocking.

As will be apparent from Table 3 and FIG. 3, in the beagles in PEP·Na-administered group, there is shown a significantly lower value of BUN in 1 day (24 hours) after release of blocking, as compared with the beagles in control group, which value reaches to a maximum after 2 days, but thereafter gradually decreases. On the other hand, in the beagles in control group, BUN continues to increase for the period of 4 days after release of blocking.

Figure 4:
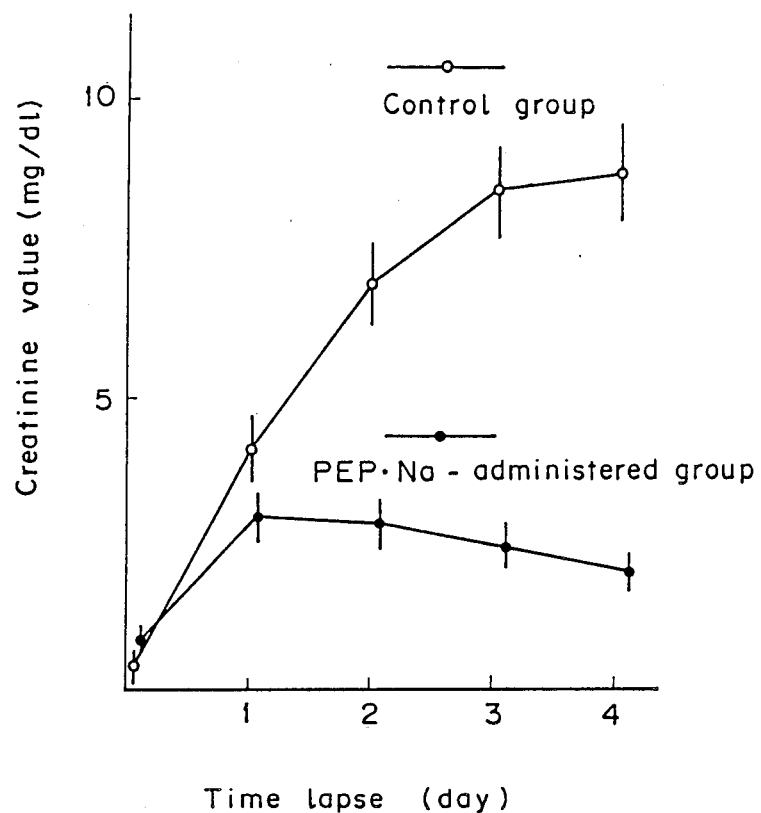
FIG. 4 is a graph showing how the value of creatinine in blood changes with time lapse when an injection comprising monosodium phosphoenolpyruvate monohydrate or a physiological saline was respectively intravenously administered to left renal arteriae of beagles by blocking them and after release of blocking.

As will be also apparent from Table 4 and FIG. 4, in the beagles in PEP·Na-administered group, there is also shown a significantly lower value of creatinine value in 1 day after release of blocking, as compared with the beagles in control group, which value gradually decreases thereafter over a period of 3 days. On the other hand, in the beagles in control group, the creatinine value continues to increase for the period of 4 days after release of blocking.

Accordingly, it has been confirmed that PEP·Na is apparently effective for the recovery of renal function of a beagle.

Test Example 3

$LD_{50}$ of monosodium phosphoenolpyruvate monohydrate to beagle

Acute toxicity ($LD_{50}$) in the case where monosodium phosphoenolpyruvate monohydrate was administered to a beagle was examined.

As a result, when monosodium phosphoenolpyruvate monohydrate was intravenously administered to a beagle, $LD_{50}$ was found to be 1,000 mg/kg or more, and, when it was orally administered, $LD_{50}$ was found to be 3,000 mg/kg or more.

Accordingly, it has been confirmed that the monosodium phosphoenolpyruvate monohydrate is a very safe substance to a living body.

As is apparent from the above, according to the process of this invention, it is possible to obtain monosodium phosphoenolpyruvate with high purity, and because of the simple procedures involved in this invention, the monosodium phosphoenolpyruvate can be produced on a industrially large scale.

Moreover, the visceral function improver of this invention is very effective for the recovery of hypofunction caused by an oxygen deficit in viscera, e.g. kidneys.

We claim:

1. A process for preparing monosodium phosphoenolpyruvate, which comprises hydrolyzing monosodium monosubstituted phosphoenolpyruvate of Formula (I):

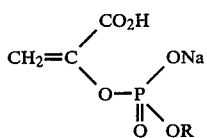

wherein, R represents $C_1$–$C_6$ alkyl group, a $C_3$–$C_{10}$ cycloalkyl group or a $C_7$–$C_{10}$ aralkyl group, with water to form said monosodium phosphoenolpyruvate.

2. The process for preparing monosodium phosphoenolpyruvate according to claim 1, further comprising adding acetone or ethanol to the resulting monosodium phosphoenolpyruvate solution to precipitate out crystals; and then the crystals obtained are dried and isolated in the form of monosodium phosphoenolpyruvate monohydrate.

3. A process for preparing monosodium phosphoenolpyruvate comprising hydrolyzing with water, to said monosodium phosphoenolpyruvate, a monosodium monosubstituted phosphoenolpyruvate of Formula (I):

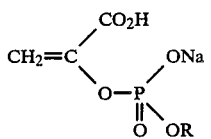

wherein R is a methyl group, an ethyl group, a n-propyl group, an isopropyl group, a n-butyl group, an isobutyl group, a sec-butyl group, a tert-butyl group, a n-amyl group, an isoamyl group, a sec-amyl group, a tert-amyl group, a n-hexyl group, an isohexyl group, a 3-methylpentyl, a neo-hexyl group or a 2,3-dimethylbutyl group; a cyclopropyl group, a cyclobutyl group, a 1-methylcyclopropyl group, a 2-methylcyclopropyl group, a cyclopentyl group, a 1-methylcyclobutyl group, a 2-methylcyclobutyl group, a 1,2-dimethylcyclopropyl group, a 2,2-dimethylcyclopropyl group, a 1-ethylcyclopropyl group, a 2-ethylcyclopropyl group, a cyclohexyl group, a 1-methylcyclopentyl group, a 2-methylcyclopentyl group, a 3-methylcyclopentyl group, a 1,2-dimethylcyclo-butyl group, a 1,3-dimethylcyclobutyl group, a 2,2- dimethylcyclobutyl group, a 2,3-dimethylcyclobutyl group, a 3,3-diemethylcyclobutyl group, a 1-ethylcyclobutyl group, a 2-ethylcyclobutyl group, a 3-ethylcyclobutyl group, 1-propylcyclopropyl group, a 2-propylcyclopropyl group, a 1-methyl-2-ethylcyclopropyl group or a 1-ethyl-2-methylcyclopropyl group; a benzyl group, a diphenylmethyl group, a triphenylmethyl group, and o-chlorobenzyl group, a p-chlorobenzyl group, a m-chloro-benzyl group, an o-methylbenzyl group, a p-methylbenzyl group or a m-methylbenzyl group.

4. The process for preparing monosodium phosphoenolpyruvate according to claim 3, wherein R is a methyl group, and ethyl group, an n-propyl group or an isopropyl group; a cyclopentyl group, a cyclohexyl group or a cycloheptyl group; or a benzyl group.

5. The process for preparing monosodium phosphoenolpyruvate according to claim 2, wherein said water is employed in an amount of 1.5 to 10 times the monosodium monosubstituted phosphoenolpyruvate employed.

6. The process for preparing monosodium phosphoenolpyruvate according to claim 2, wherein said hydrolysis is carried out at a temperature of 5° to 50° C.

7. The process for preparing monosodium phosphoenolpyruvate according to claim 6, wherein said hydrolysis is carried out for 5 to 72 hours.

8. The process of claim 3, further comprising adding acetone or ethanol to the resulting monosodium phosphoenolpyruvate solution to precipitate out crystals which are dried and isolated in the form of monosodium phosphoenolpyruvate monohydrate.

9. The process of claim 3, wherein said hydrolysis is carried out at a temperature of 5° to 50° C. for 5 to 72 hours.

10. The process of claim 9, wherein said water is employed in an amount of 1.5 to 10 times the monosodium monosubstituted phosphoenolpyruvate employed.

* * * * *